(12) United States Patent
Biswal et al.

(10) Patent No.: US 7,871,623 B2
(45) Date of Patent: Jan. 18, 2011

(54) COMPOSITIONS AND METHODS FOR IMAGING PAIN AND STRESS IN VIVO

(75) Inventors: Sandip Biswal, Stanford, CA (US); Francis G. Blankenberg, Portola Valley, CA (US)

(73) Assignee: The Board of Trustees of the Leland Stanford Junior University, Palo Alto, CA (US)

(*) Notice: Subject to any disclaimer, the term of this patent is extended or adjusted under 35 U.S.C. 154(b) by 1019 days.

(21) Appl. No.: 11/643,249

(22) Filed: Dec. 21, 2006

(65) Prior Publication Data

US 2007/0148092 A1 Jun. 28, 2007

Related U.S. Application Data

(60) Provisional application No. 60/752,566, filed on Dec. 21, 2005.

(51) Int. Cl.
*A61K 39/00* (2006.01)
*A61K 51/00* (2006.01)
*G01N 25/14* (2006.01)
*G01N 24/00* (2006.01)

(52) U.S. Cl. .................. 424/185.1; 424/1.69; 424/1.65; 424/1.11; 436/149; 436/173

(58) Field of Classification Search .................. None
See application file for complete search history.

(56) References Cited

U.S. PATENT DOCUMENTS

| | | | |
|---|---|---|---|
| 6,197,278 B1 | 3/2001 | Blankenberg et al. | |
| 6,726,895 B2 | 4/2004 | Strauss et al. | |
| 2002/0137672 A1 | 9/2002 | Kasina et al. | |
| 2003/0152513 A1 | 8/2003 | Blankenberg | |
| 2004/0170603 A1 | 9/2004 | Strauss et al. | |

OTHER PUBLICATIONS

Tait, J. et al., Structural Requirements For In Vivo Detection of Cell Death with 99mTc-Annexin V, J. Nucl Med., May 2005, 46(5); pp. 807-815.

Tarik Z. Belhocine and Francis G. Blankenberg, 99mTc-Annexin A5 Uptake and Imaging to Monitor Chemosensitivity, Methods in Molecular Medicine, pp. 363-380, vol. 111: Chemosensitivity: vol. 2: In Vivo Models, Imaging, and Molecular Regulators, Humana Press Inc., Totowa, NJ, USA, 2004. OC.

Ming Jin, Christina Smith, Heng-Yu Hsieh, Donald F. Gibson, and Jonathan F. Tait, Essential Role of B-helix Calcium Binding Sites in Annexin V-Membrane Binding, The Journal of Biological Chemistry, Sep. 24, 2004, pp. 40351-40357, vol. 279, No. 39, The American Society for Biochemistry and Molecular Biology, Inc. USA, available on line at http://www.jbc.org.

*Primary Examiner*—Olga N Chernyshev
(74) *Attorney, Agent, or Firm*—Thomas, Kayden, Horsteyemer & Risley, LLP

(57) ABSTRACT

Briefly described, embodiments of the present disclosure relate to methods and compositions for imaging pain and/or stress in a subject and methods and compositions for treating associated conditions. In particular, the present disclosure relates to the use of labeled compounds to provide objective diagnosis of pain and/or stress, for imaging regions associated with pain and/or stress, and for treating pain in a subject.

34 Claims, 7 Drawing Sheets
(3 of 7 Drawing Sheet(s) Filed in Color)

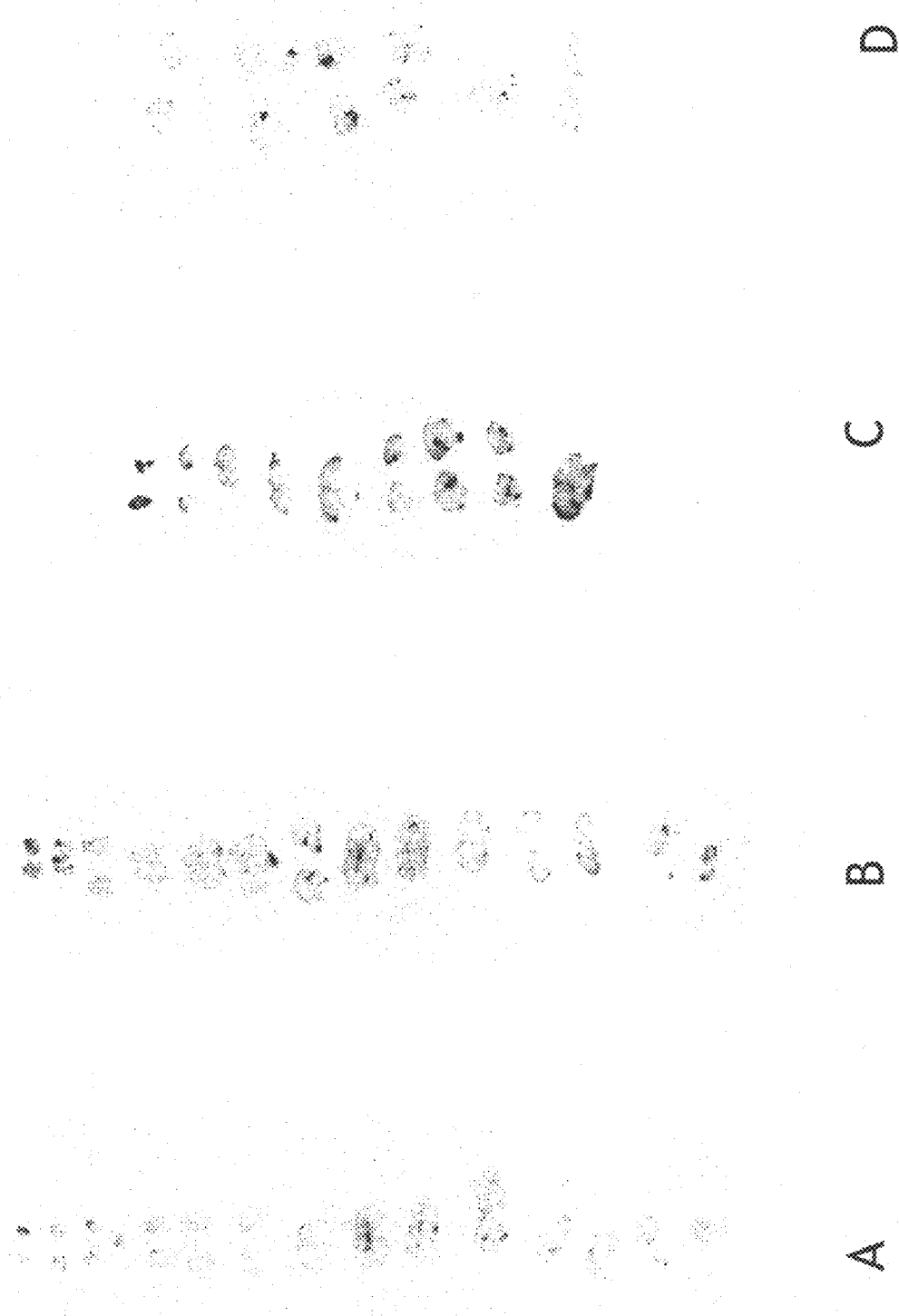

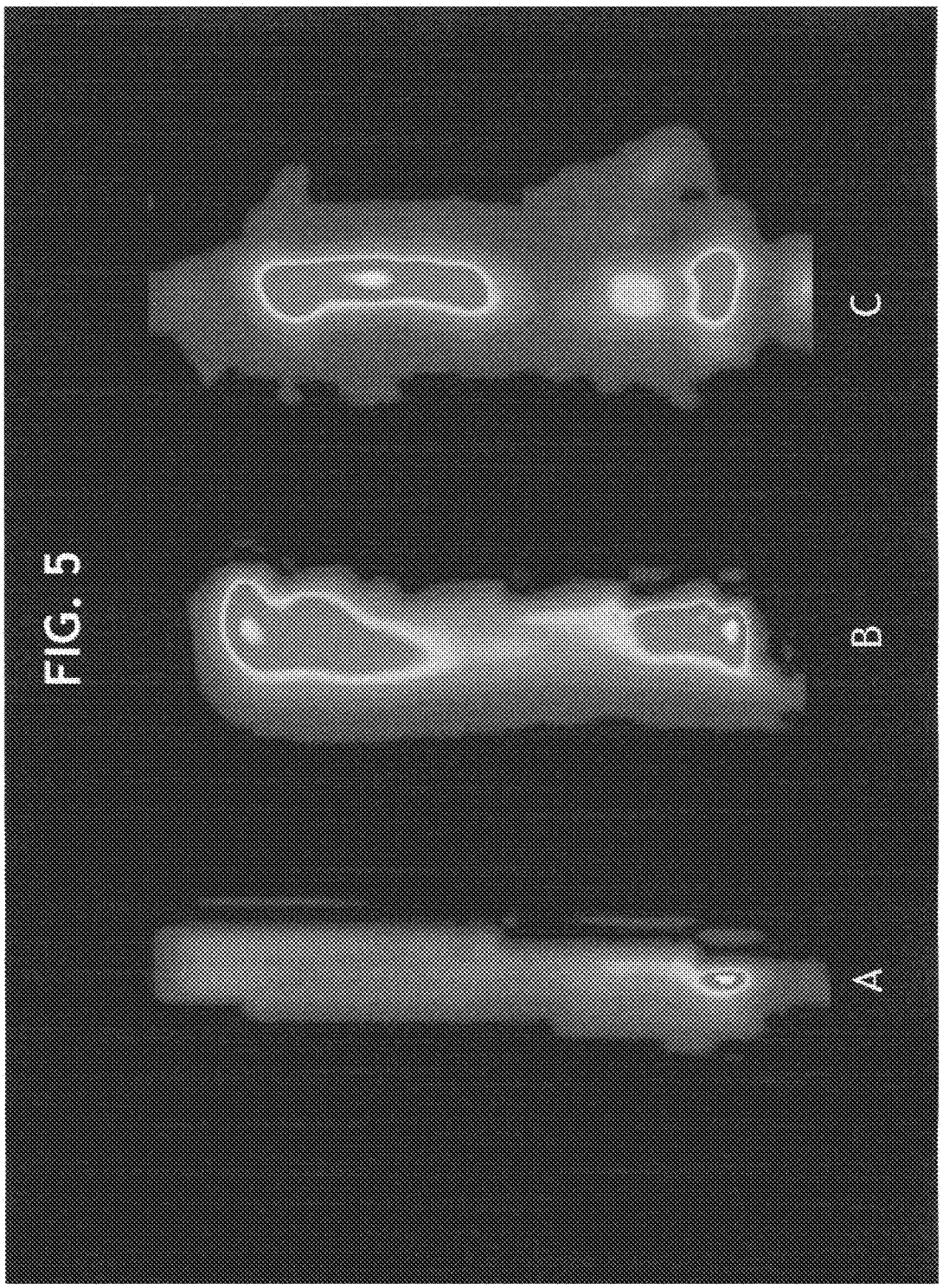

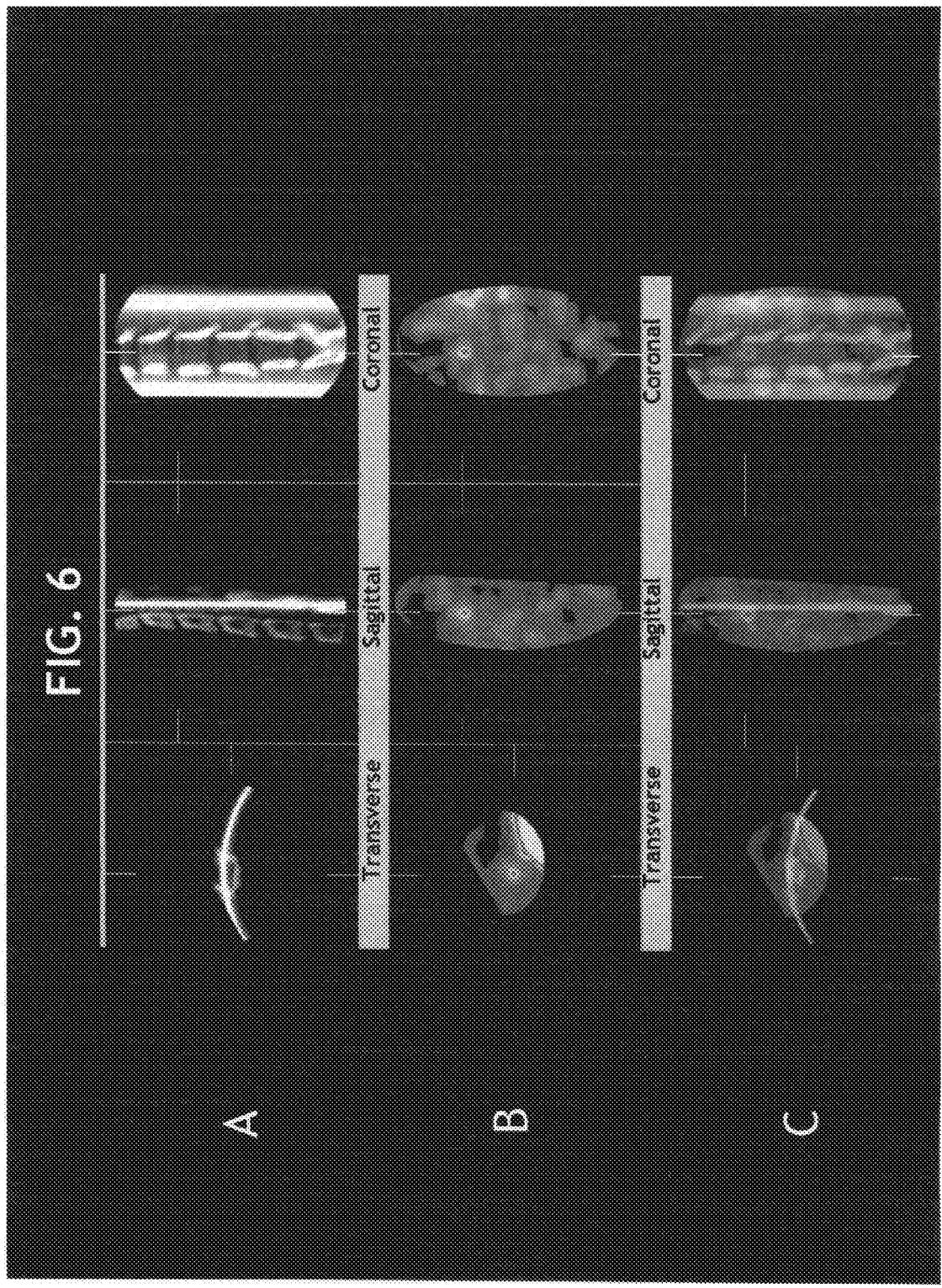

FIG. 7

SEQ ID No: 1 (Annexin V-128)

AGGCGHAQVLRGTVTDFPGFEDRADAETLRKAMKGLGTDEESILTLLTSRSNA

QRQEISAAFKTLFGRDLLDDLKSELTGKFEKLIVALMKPSRLYDAYELKHALKGA

GTNEKVLTEIIASRTPEELRAIKQVYEEEYGSSLEDDVVGDTSGYYQRMLVVLLQ

ANRDPDAGIDEAQVEQDAQALFQAGELKWGTDEEKFITIFGTRSVSHLRKVFDK

YMTISGFQIEETIDRETSGNLEQLLLAVVKSIRSIPAYLAETLYYAMKGAGTDDHT

LIRVMVSRSEIDLFNIRKEFRKNFATSLYSMIKGDTSGDYKKALLLLSGEDD

COMPOSITIONS AND METHODS FOR IMAGING PAIN AND STRESS IN VIVO

CROSS-REFERENCE TO RELATED APPLICATION

This application claims priority to and the benefit of copending U.S. provisional patent application entitled "Compositions and Methods for Imaging Pain and Stress In Vivo", Ser. No. 60/752,566 filed Dec. 21, 2005 and incorporated herein by reference in its entirety.

FEDERALLY-SPONSORED RESEARCH OR DEVELOPMENT

This invention was made with Government support under contracts EB000898 & CA102348 awarded by the National Institutes of Health. The Government has certain rights in this invention.

FIELD OF THE INVENTION(S)

The present disclosure relates to methods and compositions for imaging pain, nociception and/or stress in vivo and methods and compositions for treating associated conditions. In particular, the present disclosure relates to the use of labeled compounds to provide objective diagnosis of pain, nociception, and/or stress and for imaging regions associated with pain, nociception, and/or stress in a subject.

BACKGROUND

Currently no satisfactory, objective indicia of pain exist for determining the existence of or the extent of pain experienced by a subject. While various imaging technologies exist for the diagnosis and observation of various conditions and diseases, the capability for using such technologies for identifying and imaging pain does not currently exist. The ability of a physician to confirm a patient's complaint of pain and to determine the extent and possibly the nature and/or source of such pain would provide a significant advantage to the field of medicine in general and to the growing field of pain management in particular.

In the clinical world, physicians currently use tools such as the "Visual Analog Scale" to help determine a patient's pain experience relative to their own prior experiences. However, these evaluations cannot be normalized across human subjects. In the clinical imaging world, there are some studies using functional magnetic resonance imaging and brain positron emission tomography (PET) to image painful stimuli. However, these are restricted to the study of the brain only and do not give insight into the peripheral stimuli (a.k.a. drivers) of these unpleasant experiences.

Many patients suffer from conditions associated with atypical and/or generalized pain, such as fibromyalgia, reflex sympathetic dystrophy, peripheral nerve entrapment syndrome and chronic fatigue syndrome, where the source/cause of the pain may not be capable of determination. It can be discouraging for both the doctor and patient to be unable to confirm the patient's symptoms and/or locate the source of the pain for treatment purposes. Thus, there is a need for a technology that offers the ability to identify and measure pain and to help locate the source of the pain and/or offer treatment options. Additionally, such technology would be useful for studying various aspects of pain, such as its mechanisms, the physiological pathways associated with pain and its manifestation, and variances in the experience of pain among different subjects. Such technology would also be useful for imaging and studying conditions characterized by pain-like sensation or loss of sensation, such as spinal cord injury or compression, various neuropathies, and myelitis.

Similarly, it is difficult to objectively determine and/or measure a patient's stress level and to treat and/or prevent other medical conditions, both mental and physical, associated with elevated stress levels. The ability to image the existence of and/or the extent of stress experienced by a patient would provide numerous advantages in the field of psychiatry and psychology. This ability would provide doctors and researchers with new tools for studying the causes and physiological effects of stress, its biological manifestations, and to evaluate the effectiveness of various treatments. It may also allow detection and diagnosis of extreme or chronic stress in a subject, and thereby open the door to treating the stress before it leads to other conditions or disorders, such as hypertension, depression, and other associated conditions.

In addition, since non-human subjects are unable to communicate the existence of pain, or its source, a technology that provides the ability to image pain would offer a significant advantage in the veterinary field. It is also difficult to diagnose stress in such subjects, and not much is known about the existence, experience of or sources of stress in non-human subjects. Therefore, the ability to objectively determine the existence of stress in such subjects would provide numerous advantages, including the ability to diagnose and treat stress in non-human subjects, as well as the ability to study the condition.

SUMMARY

Briefly described, the present disclosure provides methods and compositions for imaging pain and/or stress in vivo. Aspects of the present disclosure relate to the use of labeled compounds for imaging pain and/or stress experienced by a subject and for imaging regions associated with pain and/or stress in a subject. In particular, methods of the present disclosure relate to the use of labeled annexin for imaging pain and/or stress in a subject. Other aspects of the present disclosure relate to methods and compositions for treating pain and/or stress and conditions associated with pain and/or stress.

Accordingly, embodiments of methods of imaging pain and/or stress in a subject in vivo according to the present disclosure include administering to the subject an imaging composition including annexin coupled to a biocompatible radionuclide and measuring radiation emission from the radionuclide in the subject to construct an image of radiation emission, where the image is a representation of pain and/or stress in the subject. Other embodiments include administering to the subject an imaging composition including annexin coupled to a contrast agent and obtaining a magnetic resonance image, where the image is a representation of pain and/or stress in the subject. Still other embodiments for imaging pain and/or stress in a subject include administering to the subject an imaging composition including annexin coupled to an optically active molecule, illuminating the subject with a light source, and visually monitoring the presence of the optical imaging composition in the subject, thereby obtaining an image, where said image is a representation of pain and/or stress in said subject.

Embodiments of the present disclosure also include methods for treating pain in a subject by administering to the subject a therapeutic composition comprising a pain relieving compound coupled to annexin. The present disclosure also includes embodiments of pharmaceutical compositions for treating pain in a subject where the pharmaceutical composition includes a pain relieving compound coupled to annexin.

Embodiments of the present disclosure also include kits for identifying pain and/or stress in a subject including an imaging composition of annexin coupled to a biocompatible radionuclide, a pharmaceutically acceptable carrier, and instructions for using the imaging composition to image a subject or a region of the subject to identify pain or stress experienced by the subject.

Other systems, methods, compositions, features, and advantages of the present disclosure will be or will become apparent to one with skill in the art upon examination of the following drawings and detailed description. It is intended that all such additional systems, methods, compositions, features, and advantages be included within this description, be within the scope of the present disclosure and claims.

BRIEF DESCRIPTION OF THE FIGURES

Many aspects of the disclosure can be better understood with reference to the following drawings. The components in the drawings are not necessarily to scale, emphasis instead being placed upon clearly illustrating the principles of the present disclosure.

The patent or application file contains at least one drawing executed in color. Copies of this patent or patent application publication with color drawing(s) will be provided by the Office upon request and payment of the necessary fee.

FIG. 4 shows the uptake of radiolabeled annexin V 128 in mouse brains for an old (D) and young (A and B) control mice and an old stress induced mouse (C).

FIG. 5 illustrates the uptake of radiolabeled annexin V 128 in mouse spinal cords for control mice (A) and mice with pain induced in either the left front (B) or left hind (C) paw.

FIG. 6 shows SPECT/CT images illustrating the uptake of labeled annexin-V in rat spines 24 hours after pain induction via paw injection. FIG. 6A shows a micro CT image, FIG. 6B shows a microSPECT image, and FIG. 6C shows a SPECT/CT fusion image.

FIG. 7 shows the sequence for annexin V-128, a mutated variant of human annexin V.

DETAILED DESCRIPTION

Figure 1:
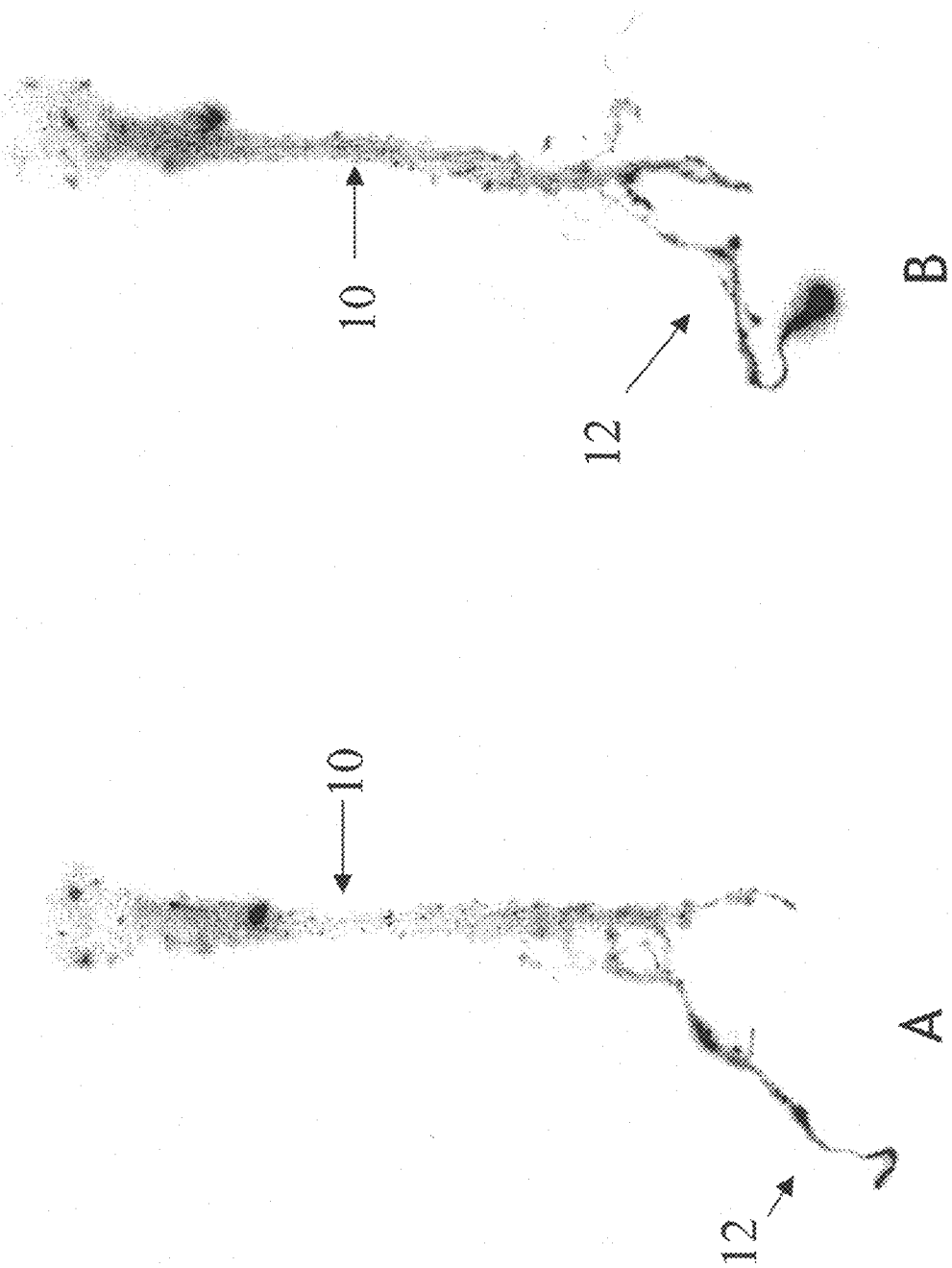
FIG. 1 shows the uptake of radiolabeled annexin V 128 in mouse spinal cords for a control (A) and pain induced (B) mouse.

Embodiments of the present disclosure will employ, unless otherwise indicated, techniques of synthetic organic chemistry, biochemistry, nuclear chemistry, molecular biology, radiology and the like, which are within the skill of the art. Such techniques are explained fully in the literature.

The following examples are put forth so as to provide those of ordinary skill in the art with a complete disclosure and description of how to perform the methods and use the compositions disclosed and claimed herein. Efforts have been made to ensure accuracy with respect to numbers (e.g., amounts, temperature, etc.) but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible. All patents, patent applications, and publications mentioned herein are hereby incorporated by reference in their entireties.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described. It must be noted that, as used in the specification and the appended claims, the singular forms "a," "an" and "the" include plural referents unless the context clearly dictates otherwise. Thus, for example, reference to "a support" includes a plurality of supports.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

In this specification and in the claims that follow, reference will be made to a number of terms that shall be defined to have the following meanings unless a contrary intention is apparent.

DEFINITIONS

As used herein, "pain" generally refers to the physiological and psychological sensation or perception of physiological pain. "Pain," as used herein, also includes nociception, the biological experience of pain that is mediated through receptors and neurotransmitters and other aspects of the nervous system. Thus, as used herein, "imaging pain" refers to a form of visual indication of the perception of physiological pain by the subject imaged. "Pain" may be specifically located to a site of injury, or may be generalized; likewise, and image of pain may visually indicate a general state of pain perception or it may specifically indicate the location of the pain or source of pain.

As used herein, "stress" generally refers to a psychological sensation or perception of a strong psychological condition and the physiological response thereto. Although stress includes both positive (eustress) and negative (distress) stress as used, herein, stress generally refers to an extreme (positive or negative) condition and/or a generally unpleasant mental condition (distress). Examples of stress include, but are not limited to, psychological pain, fear, anxiety, excitement, panic, and the like. Although considered a psychological state, stress generally has physiological origins and/or manifestations. As used herein, "imaging stress" refers to a form of visual indication of the perception or sensation of a stressful mental/physical condition by the subject imaged.

A "biocompatible radionuclide" or "biocompatible radioisotope" refers to an isotope that is recognized as being useful for injection into a patient for nuclear medicine applications. Examples of biocompatible radionuclides include, but are not limited to, Iodine 123, Iodine 131, Gallium 67, Indium 111, Fluorine 18, and Technetium 99 m.

As used herein, an "optically active molecule" includes any molecule that has the ability to be optically detected, for example, by the use of medically available visualization devices such as endoscopes, bronchoscopes and minimally invasive surgical devices using optical detection of anatomic structures. Examples of optically detectable molecules include fluorescein and methylene blue. Optically active molecules may also include those agents useful in photodynamic therapy (PDT). PDT works by exposing an annexin molecule linked to a photosensitizing molecule to specific wavelengths of light in the presence of oxygen. When this reaction occurs, the normally innocuous photosensitizing drug becomes cytotoxic via an activated species of oxygen, known as singlet oxygen. Examples of optically active agents that could be used in PDT when linked to annexin include PHOTOFRIN®, Lutrin, ANTRIN®, FOSCAN®, aminolevulinic acid, aluminum (III) phthalocyanine tetrasulfonate, Hypericin, verteporfin, and methylene blue dye.

As used herein, a "contrast agent" is intended to include any agent that is physiologically tolerable and capable of providing enhanced contrast for magnetic resonance imaging. Contrast agents typically have the capability of altering the response of a tissue to magnetic fields. Contrast agents include paramagnetic agents, e.g., a gadolinium-chelating group complex, such as gadolinium-diethylenetriamine penta-acetic acid, or a manganese chelating group complex; or biologically compatible superparamagnetic agents, such as iron oxide. Contrast agents, such as those described in U.S. Pat. No. 4,687,658; U.S. Pat. No. 5,314,680; and U.S. Pat. No. 4,976,950 can be used in preparing the compositions of the present disclosure, and are included herein by reference. Contrast agents are commercially available (e.g., the gadolinium chelate Prohance™ is available from Squibb and the gadolinium chelate Dotarem™ is available from Guerbet).

A suitable contrast agent is preferably biocompatible, e.g., non-toxic, chemically stable, not absorbed by the body or reactive with a tissue, and eliminated from the body within a short time. In one embodiment, the contrast agent may be coupled to a carrier that is cleared or metabolized by a desirable route. Examples of such carriers include, but are not limited to, dextran particles or colloidal particles (which are typically phagocytosed in the liver).

As used herein, the term subject includes animals, preferably warm-blooded animals, more preferably mammals, including humans. In a preferred embodiment, the subject is a primate. In an even more preferred embodiment, the subject is a human. Pain or stress may be imaged or detected in, for example, an organ of a subject or a portion or specimen thereof (e.g., brain, spinal cord, heart, liver lung, pancreas, and colon) or a gland of a subject or a portion thereof (e.g., prostate, pituitary or mammary gland).

As used herein, the term "administering" to a subject includes dispensing, delivering or applying an imaging composition according to the present disclosure to a subject by any suitable route for delivery of the composition to the desired location in the subject. The preferred route of administration of the compounds is intravenous. However, any route of administration, such as oral, topical, buccal, parenteral, subcutaneous, peritoneal, intraarterial, intralymphatic, insulation, intramuscular, intrapleural, inhalation, intrathecal, transdermal, vaginal, rectal, colonic, nasal, introduction into the cerebrospinal fluid, or instillation into body compartments can be used.

The compositions of the disclosure may be administered to a subject in an amount effective to achieve the desired result at the appropriate dosages and for the desired periods of time. An effective amount of the compositions of the disclosure may vary according to factors such as disease state, age, and weight of the subject, and the ability of the composition to elicit a desired response in the subject. An effective amount is also one in which any toxic or detrimental effects (e.g., side effects) of the compositions are outweighed by the therapeutically or diagnostically beneficial effects. The compositions of the disclosure may be administered at a concentration of, for example, about 1-1000 µg protein/kg, about 1-900 µg protein/kg, about 1-800 µg protein/kg, about 1-700 µg protein/kg, about 1-600 µg protein/kg, about 1-500 µg protein/kg, about 1400 µg protein/kg, about 1-300 µg protein/kg, about 1-200 µg protein/kg, about 1-100 µg protein/kg, about 10-100 µg protein/kg, about 10-80 µg protein/kg, about 10-60 µg protein/kg, about 1040 µg protein/kg, or about 10-20 µg protein/kg.

As used herein, "treat", "treating", and "treatment" are an approach for obtaining beneficial or desired clinical results. For purposes of embodiments of this disclosure, beneficial or desired clinical results include, but are not limited to, preventing the condition/disease from occurring in a subject that may be predisposed to the condition/disease but does not yet experience or exhibit symptoms of the disease (prophylactic treatment), alleviation of symptoms of the condition/disease, diminishment of extent of the condition/disease, stabilization (i.e., not worsening) of the condition/disease, preventing spread of the condition/disease, delaying or slowing of the condition/disease progression, amelioration or palliation of the condition/disease state, and combinations thereof. Thus, treating pain refers to the reduction and/or elimination of actual and/or perceived pain in a subject receiving treatment and/or the reduction of annexin uptake in the subject.

The terms "including", "such as", "for example" and the like are intended to refer to exemplary embodiments and not to limit the scope of the present disclosure.

Discussion:

Annexin and the Asymmetry of Biological Membranes

Annexin V is normally found in high levels in the cytoplasm of a number of cells including placenta cells, Lymphocytes, monocytes, and biliary and renal (cortical) tubular epithelium. Although the physiological function of annexins has not been fully elucidated, several properties of annexins make them useful as diagnostic and/or therapeutic agents. In particular, it has been discovered that annexins possess a very high affinity for anionic phospholipid surfaces, such as a membrane leaflet having an exposed surface of phosphatidylserine (PS), which is significant for the imaging of pain and stress as explained in greater detail below.

It is generally believed that biological membranes are asymmetric with respect to specific membrane phospholipids. In particular, the outer leaflet of eukaryotic plasma membranes is formed predominantly with the cholinephospholipids, such as sphingomyelin and phosphatidylcholine (PC), whereas the inner leaflet contains predominantly aminophospholipids, such as phosphatidylserine (PS) and phosphatidylethanolamine (PE). This asymmetry is thought to be maintained by the activity of an adenosine triphosphate (ATP)-dependent aminophospholipid translocase, which selectively transports PS and PE between bilayer leaflets. Other enzymes thought to be involved in the transport of phospholipids between leaflets include ATP-dependent floppase and lipid scramblase.

Although asymmetry appears to be the rule for normal cells, the loss of such asymmetry is associated with certain physiological processes, as well as pathogenic processes. For example, it has been recognized that membrane asymmetry, detected as the appearance of PS on the outer leaflet of the plasma membrane ("PS exposure"), is one of the earliest manifestations of apoptosis, preceding DNA fragmentation, plasma membrane blebbing, and loss of membrane integrity.

Similar re-orientation has been observed in sickle cell disease B-thalassemia, platelet activation, and in some mutant tumor cell lines with defective PS transport. A gradual appearance of PS on the outer leaflet has also been observed to occur in aging red blood cells. When the PS exposure on such cells reaches a threshold level, the cells are removed from circulation by macrophages. All of the above conditions proximately culminate in the death of the affected cells (e.g., cells with significant PS exposure).

However, the examples presented below demonstrate the unexpected result that PS exposure occurs, along with the associated increased uptake of annexins, during periods of cell stress (such as that induced by pain or mental stress experienced by a subject) that do not necessarily lead to a commitment to apoptosis and the self-destruction of a cell. Annexins can also be selectively taken up in the neurons of regions of ischemia and stress, even in the presence of an intact blood brain barrier.

Imaging Pain and Stress

Annexins, particularly annexin V, has been demonstrated as a useful in vivo imaging marker for apoptosis and/or necrosis, as described in U.S. Pat. Nos. 6,197,278 and 6,726,895 and in Published U.S. Applications 20040170603, 20030152513, and 20030003047, which are each incorporated herein by reference in their entirety. However, it has presently been discovered, as demonstrated in the examples below, that annexins are also taken up by non-apoptotic cells, particularly in tissues of the peripheral and central nervous system as well cells of the vascular system, when such cells are responding to stimuli caused by pain, stress, or other noxious stimuli.

Thus, the present disclosure provides methods for using annexin labeled with various imaging compounds, such as, but not limited to, isotopes, fluorochromes and magnetic resonance agents to image acute and/or chronic pain in vivo. Other embodiments of the present disclosure provide using the labeled annexin to image stress in vivo.

The ability to image pain and/or stress provides objective indicia of those conditions, as well as the possibility of determining the degree and/or intensity of the pain and/or stress. For pain, it also may allow the location of the source or origin of the pain, if not apparent from examining the subject. The methods of the present disclosure also provide the ability to target, diagnose, and/or research various disorders associated with pain and/or stress. This includes atypical pain syndromes such as, but not limited to, fibromyalgia, chronic fatigue syndrome, reflex sympathetic dystrophy, and peripheral nerve entrapment syndrome. The methods can also be used to detect and study conditions and/or disorders that cause stress on the neurological system such as, but not limited to, depression, physical stress, mental stress, and stress caused by hormonal imbalances (e.g., estrogen, progesterone, thyroid hormones, insulin, various steroids, and the like). The ability to image stress associated with such disorders provides not only new avenues for understanding the mechanisms and effects of the disease, but also new tools for designing and testing new therapies for treating such diseases and conditions.

Other conditions related to the central and peripheral nervous system that could also be targeted by use of the methods of the present disclosure include, but are not limited to, myelitis (e.g., caused by radiation treatment, chemotherapy, infection, post-infectious transverse myelitis, etc.), spinal cord injury (for instance, predicting reversible vs. irreversible lesions based on uptake of labeled annexin), neuropathy (e.g., that associated with Guillain-Barre syndrome, ALS, and other neurologic disorders with peripheral manifestations such as Parkinsons, Dyskinesias, Alcoholism, and Diabetes), and spinal cord compression (e.g., the chronic conditions caused by disc disease and spinal stenosis).

The methods of the present disclosure are useful with various imaging technologies including, but not limited to, radiation emission imaging, optical imaging, and magnetic resonance imaging. Various embodiments of these methods are described in greater depth below.

Synthesis of Annexin Containing Compounds

The methods and compositions of the present disclosure can be practiced using purified native, recombinant, or synthetically-prepared annexin. Annexin V, for example, may be conveniently purified from human placenta. Recombinant annexin offers several advantages, however, including ease of preparation and economic efficiency. A number of different annexins have been cloned from humans and other organisms. Their sequences are available in sequence databases, including GenBank.

Preferably the annexin used for practicing the methods of the present disclosure is annexin V, for several reasons. First, annexin V is one of the most abundant annexins, (ii) it is simple to produce from natural or recombinant sources, and (iii) it has a high affinity for phospholipid membranes. Human annexin V has a molecular weight of 36 kD and high affinity (kd=7 nmol/L) for phosphatidylserine (PS). The sequence of human annexin V can be obtained from GenBank under accession numbers U05760-U05770. Annexin V is typically administered at doses less than about 300 µg protein/kg, preferably between about 1 and 10 µg protein/kg. Several administration routes are possible, including intravenous (i.v.), intraperitoneal (i.p.), intrathecal, and intrapleural administration.

Even more preferably, the annexin is annexin V-128. Annexin V-128 (SEQ ID NO: 1, FIG. 7) is a modified annexin V having an endogenous radionuclide (e.g., Tc) chelation site (Ala-Gly-Gly-Cys-Gly-His) (amino acids 1 to 6 of SEQ ID NO: 1) added to the N-terminus. Annexin V-128 has the same or higher uptake as wild type annexin V, except that it has 88% lower renal uptake. Methods of making annexin V-128 and other information related to its uptake are described in Tait J F, Smith C, Blankenberg F G; *Structural Requirements for In vivo Detection of Cell Death with 99 mTc-Annexin V*; J. Nucl. Med. 2005; 46; 807-815, which is hereby incorporated by reference.

An exemplary expression system suitable for making annexin for use with the present disclosure employs the pET12a expression vector (Novagen, Madison, Wis.) in *E. coli.* (described in Wood, et al. (1996) *Blood* 88:1873-1880, incorporated herein by reference). Other bacterial expression vectors and other commercially-available expression systems, such as yeast expression systems, may be utilized as well.

Annexin produced as described above may then be coupled to a radionuclide, a contrast agent, an optically active molecule, and/or an analgesic compound. The particular radionuclide, the contrast agent, the optically active molecule, or the analgesic compound selected will depend on the particular application the skilled artisan intends to use.

Radiolabeled Imaging

Embodiments of the present disclosure include methods of imaging pain and/or stress in a subject, particularly a mammalian subject, in vivo using annexin labeled with a radionuclide. The method includes administering annexin labeled with a biocompatible radionuclide to the subject. After a period of time in which the labeled annexin can achieve localization in the subject, the subject is positioned within the detection field of a radiation detector device, and radiation emission from the radionuclide localized in the subject is measured with the radiation detector device. The radiation detector device then constructs an image of radiation emission, where the image is a representation of pain and/or stress experienced by the mammalian subject. In one embodiment, the method further includes a step of processing the image to subtract signal resulting from non-specific localization of the labeled annexin, such as non-specific localization in the kidney.

The annexin may be coupled with any one of a variety of radionuclides presently available. In selecting a suitable radionuclide, the practitioner typically considers the particular application, along with factors common to nuclear imaging in general. Such factors include minimum of particle emission, primary photon energy of between about 50 and 500 kEv, physical half-life greater that the time required to prepare material for administration, effective half life longer than the examination time, suitable chemical form and reactivity, low toxicity, and stability at or near the stability of annexin labeled with that radionuclide.

Radionuclides useful with the method include, but are not limited to, Iodine 123, Iodine 131, Iodine 125, Iodine 124, Carbon 11, Chlorine 32, Chlorine 33, Chlorine 34, Bromine 74, Bromine 75, Bromine 76, Bromine 77, Bromine 78, Rhenium 186, Rhenium 188, Yttrium 90, Yttrium 86, Samarium 153, Lutetium 177, Gallium 67, Indium 111, Fluorine 18, and Technetium 99 m (Tc99m). It is appreciated that Fluorine 18 is a positron emitter, and is thus useful in positron emission tomography (PET). Other compounds useful in PET include, but are not limited to, Cu-64 (PET emitting isotope of copper), Ga-68 (PET emitting isotope of Gallium), Tc-94 (PET emitting isotope of technetium), and I-124 (PET emitting isotope of iodine). Iodine 123, Iodine 131, Gallium 67, Indium 111, and Technetium 99 m (Tc99m) are useful with standard gamma emission detection. Tc99m is a preferred radionuclide for use with the methods of the disclosure. In a preferred embodiment, the Tc99m is linked to the annexin via hydrazino nicotinamide (HYNIC). Tc99m-labelled annexin is typically administered at a dose of about 5 to about 20 mCi.

Linking of the isotope to annexin can be accomplished using known techniques. For example, Tc99m can be linked to annexin through the use of a hydrazino nicotinamide (HYNIC) group, available, e.g., from AnorMED, Langley, British Columbia, Canada, as described in the examples below. Gallium 67 and Indium 111 can be used to radiolabel proteins using, for example, the method described by Hnatowich, et al., *The Preparation of DTPA-Coupled Antibodies Radiolabeled With Metallic Radionuclides: an Improved Method.* J Immunol Methods. 1983 Dec. 16; 65(1-2):147-57.), incorporated herein by reference.

Other methods for labeling proteins with radionuclides are known. For example, U.S. Pat. No. 5,552,525, which is hereby incorporated by reference herein, teaches the making of technetium-99m (Tc-99m) labeled peptides. Methods for labeling peptides and polypeptides with Tc-99m are also disclosed in U.S. Pat. Nos. 5,443,815 and 5,508,020, which are hereby incorporated by reference herein. Additional methods for labeling polypeptides with Tc-99m are described in the following references, which are hereby incorporated by reference in their entireties: Lind, et al., *Immunoscintigraphy of Inflammatory Processes With a Technetium-99m-labeled Monoclonal Antigranulocyte Antibody (MAb BW 250/183)*, J Nucl Med. 1990 April; 31(4):417-23 (Tc-99m labeled monoclonal antibodies); LaMuraglia, et al., *Utility of the indium 111-labeled human immunoglobulin G scan for the detection of focal vascular graft infection.* J Vasc Surg. 1989 July; 10(1):20-7 ($^{111}$In-labeled non-specific human immunoglobulin); and Fischman, et al., *Imaging focal sites of bacterial infection in rats with indium-111-labeled chemotactic peptide analogs.* J Nucl Med. 1991 March; 32(3):483-91 (chemotactic formyl peptide (fMLF) in-labeled DTPA conjugates).

Radiolabeled annexin may be administered using standard protocols for administration of radiolabeled compounds. The amounts include the ranges listed above, but individual dosages will vary based on various considerations. The dosage generally relates to two considerations: (i) the amount and type of radionuclide injected, and (ii) the amount of annexin protein injected. Technetium 99m can be administered to adult humans at doses up to about 20 mCi. The preferred dose for a single Tc99m administration is between about 5 and 20 mCi.

Annexin V begins to have pharmacological effects (anticoagulant effects) at doses greater than about 300 µg/kg. Accordingly, the diagnostic methods of the present disclosure (which seek to generally avoid pharmacological effects of the labeled annexin) are preferably practiced at doses lower than about 300 µg/kg, typically less than about 50 µg/kg. Such tracer doses (e.g., 10 µg/kg to 50 µg/kg) have no reported pharmacologic or toxic side effects in animal or human subjects.

The radiolabeled annexin is typically suspended in a suitable delivery vehicle/pharmaceutically acceptable carrier, such as sterile saline. The vehicle may also contain stabilizing agents, carriers, excipients, stabilizers, emulsifiers, and the like, as is recognized in the art.

Radiolabeled annexin can be administered by any of several routes known to be effective for administration of radiolabeled proteins for nuclear medicine imaging. A preferred method of administration is intravenous injection (i.v.). It is particularly suitable for imaging of well-vascularized internal organs, such as the heart, liver, spleen, etc. Methods for i.v.

injection of radiopharmaceuticals are known. For example, it is recognized that a radiolabeled pharmaceutical is typically administered as a bolus injection using either the Oldendorf/Tourniquet method or the intravenous push method (see, e.g., Mettler and Guierbteau, 1985, Essentials Of Nuclear Medicine Imaging, Second Edition, W.B. Saunders Company, Philadelphia, Pa.). For imaging the brain, the labeled annexin can be administered intrathecally. Intrathecal administration delivers compound directly to the sub-arachnoid space containing cerebral spinal fluid (CSF). Delivery to spinal cord regions can also be accomplished by epidural injection to a region of the spinal cord exterior to the arachnoid membrane.

Other modes of administration include intraperitoneal (e.g., for patients on kidney dialysis), and intrapleural administration. For specific applications, this disclosure contemplates additional modes of delivery, including intramuscular injection, subcutaneous, intralymphatic, insufflation, and oral, intravaginal and/or rectal administration. Methods for practicing the modes of administration listed above are known in the art.

After the labeled annexin is administered, it is allowed to localize to the target tissue or organ. Localization in this context refers to a condition when either an equilibrium or a pseudo-steady state relationship between bound, "localized", and unbound, "free" labeled annexin within a subject has been achieved. The amount of time for such localization to occur is typically on the order of minutes to tens of minutes. It can be estimated by the serum half-life of the labeled annexin. In the case of Tc99m-labeled annexin V injected i.v., the serum half life is between about 3 and 7 minutes. The localization time also depends on the accessibility of the target tissue to the labeled annexin. This in turn depends on the mode of administration, as is recognized in the art. A reasonable estimate of the time to achieve localization may be made by one skilled in the art. Furthermore, the state of localization as a function of time may be followed by imaging the gamma ray signal from the labeled annexin according to the methods of the present disclosure.

In one general embodiment of the present disclosure, the radiation detector device is a gamma ray detector device, and the measured radiation emission is gamma ray emission. In another general embodiment, the radiation detector device is a positron emission detector device and the measured radiation emission is positron emission. The radiation detector device may be, for example, an Anger gamma scintillation camera or a 3-dimensional imaging camera.

In yet another general embodiment, the method of imaging pain and/or stress in a subject further includes repeating the steps of positioning the subject within the detection field of a radiation detector device and measuring radiation emission from the radionuclide to create an image of the radiation emission at selected intervals, where the repeating is effective to track changes in the intensity of radiation emission (e.g., gamma ray or positron emission) from the region over time, reflecting changes in the intensity of the pain as demonstrated by the degree of uptake of labeled annexin.

Still another general embodiment includes repeating the steps above at selected intervals, where the repeating is effective to track changes in the localization of gamma ray emission in the region over time, reflecting changes in the location of cells reacting to the pain or stress stimuli. For instance, as FIG. 1 demonstrates, annexin uptake can be tracked to the pain source at the left hindpaw.

The measuring of gamma ray emission to construct an image is typically done between about 5 minutes and 2 hours after administration of the labeled annexin. In one embodiment, the measuring of gamma ray emission to construct the image is done about 1 hour after administration of the labeled annexin.

Different portions of the subject may be imaged using the method disclosed herein. For example, the region may include substantially the whole subject, or a portion of the subject, such as the head or portion thereof, the heart or portion thereof, the liver or portion thereof, and the like. Preferably, the region imaged includes the brain and/or spinal cord, as the pattern for pain and/or stress induced uptake tends to involve the entire neuro-axis and is not limited to particular neural pathways.

Images generated by methods of the present disclosure may be analyzed by a variety of methods. They range from a simple visual examination, mental evaluation and/or printing of a hardcopy, to sophisticated digital image analysis.

Additional details regarding the synthesis of radiolabeled annexin, administration of the radiolabeled annexin composition to a subject, localizing the radiolabeled annexin, and creating and processing the images, are described in U.S. Pat. No. 6,197,278, which is incorporated by reference above.

Magnetic Imaging

In another aspect, the present disclosure provides a method for the in vivo imaging of pain and/or stress in a subject, preferably a mammalian subject, by administering to the subject a magnetic resonance imaging composition including annexin coupled to a contrast agent. Then a magnetic resonance image is obtained, wherein the image is a representation of pain and/or stress in the mammalian subject.

Contrast agents useful in practicing the methods of the present disclosure include, but are not limited to, paramagnetic agents (e.g., a gadolinium-chelating group complex, such as gadolinium-diethylenetriamine penta-acetic acid, or a lanthanum chelating group complex) or superparamagnetic agents (e.g., a metal oxide, such as Fe, Co, Ni, Cu, Zn, As, Se, Mo, Tc, Ru, Rh, Pd, Ag, Cd, In, Sn, Re, Os, Ir, Pt, Au, Hg, Tl, Pb, Bi, Po, or At oxide). The metal oxide is preferably coated with a polymer, e.g., dextran or variants thereof. The annexin may be coupled (e.g., chemically, biologically, or a combination thereof) to the contrast agent directly or indirectly.

In another embodiment, the contrast agent may be a polymer coated metal oxide, and a radioisotope, e.g., a diagnostic or therapeutic radioisotope. Such compositions are suitable for both MRI and nuclear medicine imaging. For example, the composition may include annexin V coupled to a contrast agent and a radioisotope (linked to the annexin via hydrazino nicotinamide (HYNIC)). In one embodiment, the annexin may be coupled to a carrier that is cleared or metabolized by a desirable route. Examples of such carriers include, but are not limited to, dextran particles or colloidal particles or metal oxide particles, such as superparamagnetic iron oxide particles (which are typically phagocytosed in the liver).

The magnetic resonance image may be obtained using any of the art known techniques, for example, using a Picker Corp. Whole Body Superconducting System operating at 0.3 T using a 30 cm transmitter coil tuned to 0.26 T (10.08 MHz) or other MRI devices with field strengths ranging from 0.05 Tesla to 4.0 Tesla. Typically, the subject is placed in a powerful, highly uniform, static magnetic field. Magnetized protons (hydrogen nuclei) within the subject align like small magnets in this field. Radiofrequency pulses are then utilized to create an oscillating magnetic field perpendicular to the main field, from which the nuclei absorb energy and move out of alignment with the static field, in a state of excitation. As the nuclei return from excitation to the equilibrium state, a signal induced in the receiver coil of the instrument by the nuclear magnetization can then be transformed by a series of algorithms into images. Images based on different tissue characteristics can be obtained by varying the number and sequence of pulsed radiofrequency fields in order to take advantage of magnetic relaxation properties of the tissues.

If it is desired to follow the localization and/or the signal over time, for example, to record the effects of a treatment on the intensity, distribution and/or localization of cells responding to pain or stress, the imaging can be repeated at selected time intervals to construct a series of images. The intervals can be as short as minutes, or as long as days, weeks, months or years. Images generated by methods of the present disclosure may be analyzed by a variety of methods. They range from a simple visual examination, mental evaluation and/or printing of a hardcopy, to sophisticated digital image analysis.

The magnetic resonance image may be obtained about 5, 10, 15, 20, 25, 30, 35, 40, 45, 50, 55, 60, 65, 70, 75, 80, 85, 90, 95, 100, 105, 110, 115, or 120 minutes after the administration of the magnetic resonance imaging composition to the subject. In another embodiment, the magnetic resonance image is obtained about 10-30, 15-25, 20-25, or 20-30 hours after the administration of the magnetic resonance imaging composition to the subject. Ranges intermediate to the above-recited values are also intended to be part of this disclosure. For example, ranges using a combination of any of the above-recited values as upper and/or lower limits are intended to be included. In a preferred embodiment, the magnetic resonance image is obtained at a plurality of time points, thereby monitoring changes in the number of cells responding to pain and/or stress, or monitoring changes in the location of cells responding to pain and/or stress.

Coupling of Annexin to Contrast Agents

Coupling of annexin to contrast agents may be performed using any of the art known techniques, e.g., chemical chelation techniques. Coupling of annexin to a metal oxide may be performed as described in *Chelating Agents and Metal Chelates*, Dwyer & Mellor, Academic Press (1964), Chapter 7 and U.S. Pat. No. 5,443,816, the contents of each of which are incorporated herein by reference. Ionic forms of the elements iron, cobalt, nickel, copper, zinc, arsenic, selenium, technetium, ruthenium, palladium, silver, cadmium, indium, antimony, rhenium, osmium, iridium, platinum, gold, mercury, thallium, lead, bismuth, polonium, and astatine, among others may be used.

For example, annexin may be incubated with a first reducing agent for a period sufficient to reduce available disulfide bonds to thiolate groups while preventing excessive fragmentation of the annexin. The first reducing agent may then be substantially removed from the thiolate-containing annexin and a source of Sn (II) agent may then be added to the thiolate-containing annexin in a sufficient amount to form Sn (II)-containing and sulfur-containing complexes. The Sn (II)-containing and sulfur-containing complexes may then be labeled by adding the metal oxide, whereby the metal oxide displaces the Sn (II) agent and the metal oxide and thiolate-containing annexin form a complex. The order of the foregoing steps may be altered. For example, it is possible, and in some cases advantageous, to add the Sn (II) to form Sn (II)-containing and sulfur-containing complexes prior to removing excess reducing agent from the thiolate-containing annexin. In this way, oxidation of thiolate groups or reformation of disulfide bonds and other cross-linkages can be minimized.

A compound of the disclosure may be created by associating annexin with biodegradable superparamagnetic metal oxides such as iron oxide. Annexin associated with superparamagnetic or paramagnetic contrast agents provides the advantage of directing the magnetic resonance contrast agent to those cells that are stressed (e.g., expressing PS but not apoptotic), apoptotic or necrotic, or in the methods of the present disclosure, to those cells or regions of a subject identified with pain and/or stress. A compound prepared from annexin and biodegradable superparamagnetic iron oxide, for example, binds to hepatocytes that are rendered apoptotic by treatment with fas. A magnetic resonance experiment or imaging procedure carried out after administration to a subject of the compounds of the disclosure can, thus, provide a method for obtaining an enhanced magnetic resonance image, as well as valuable information regarding the distribution and/or intensity of pain and/or stress in the subject. Annexin can be labeled with biodegradable superparamagnetic metal oxides for MR imaging by procedures known to those of skill in the art (e.g., as described in Hiller et al., Assessment of cardiovascular apoptosis in the isolated rat heart by magnetic resonance molecular imaging. Mol Imaging. 2006 April-June; 5(2):115-21; van Tilborg et al., Annexin A5-functionalized bimodal lipid-based contrast agents for the detection of apoptosis. Bioconjug Chem. 2006 May-June; 17(3):741-9; and Sosnovik et al., Magnetic resonance imaging of cardiomyocyte apoptosis with a novel magneto-optical nanoparticle. Magn Reson Med. 2005 September; 54(3):718-24, each of which are hereby incorporated by reference in their entireties).

The use of magnetic particles for the attachment of biomolecules has been described by Molday (U.S. Pat. No. 4,452,773, the entire contents of which are incorporated herein by reference). Briefly, a dextran coated magnetic particle is formed and then treated with periodate to produce aldehyde groups. The aldehydes react with amino groups on a biological molecule, to form a Schiff base. The Schiff base may be stabilized by treatment with a reducing agent like sodium borohydride. After treatment with a reducing agent a methylene amino linker connects the biomolecule to the nanoparticle. Other methods of attaching biomolecules to nanoparticles, which use the reactivity of the aldehyde group, may also be used, including the methods of Rembaum and Owen (see Table I).

The development of amine functionalized crosslinked iron oxide nanoparticle is another method of synthesizing magnetic particle-biomolecule conjugates that may be used to attach annexins to a metal oxide particle. Amino-CLIO is prepared by first synthesizing a dextran coated magnetic nanoparticle, followed by crosslinking the dextran with epichlorohydrin. Amine groups are incorporated by reacting the dextran with ammonia.

Table I (below) summarizes the types of magnetic particles that may be used for the attachment of annexins, e.g., annexin V and annexin V-128.

TABLE I

Magnetic Particles That Can Be Used for the Attachment of Annexins

| Particle Size | Attachment Chem/ Biomolecule Attached | Polymer | Reference |
| --- | --- | --- | --- |
| <100 nm | Periodate/antibody | Dextran | Abts (1989) J. Immunol Methods 125, 19. |
| 10-70 nm/dextran | Periodate/antibody | Dextran | U.S. Pat. No. 4,452,773 (Molday); Molday, (1982) J. Immunol. Methods 52, 353. |
| 10-200 nm/albumin | SPDP/antibody | BSA | U.S. Pat. No. 4,795,698 (Owen). |
| 10-50 nm | Periodate/Synaptotagmin 1 | Carboxy Dextran | Zhoe (2001) Nat. Med. 7, 1241. |
| 40 nm | SPDP.Oligonucleotides and Peptides | Crosslinked Dextran | Josephson (1999) Bioconjug. Chem. 10, 186. |
| 10-200 nm | Aldehydes/Enzymes, Biomolecules | Polyglutaraldehyde Polymer | U.S. Pat. No. 4,438,239 (Rembaum) U.S. Pat. No. 4,369,226. |
| 10-100 nm | Periodate/Antibody | Dextran | U.S. Pat. No. 5,492,814 (Weissleder) |

The conjugation of annexins to magnetic molecules yields materials that can be used in a variety of fields such as magnetic affinity chromatography, magnetic cell sorting, magnetic immunoassay, and as MR imaging contrast agents. The preferred characteristics of the particle vary greatly with the intended application. For imaging applications, the magnetic particles preferably have one or more of a series of properties including:

(1) Size and size homogeneity. Magnetic particles are preferably smaller than the size of red blood cells (about 10 microns) to avoid clogging capillary beds. To achieve efficient targeting to a target cell or organ after injection, they are preferably in the nanoparticle size range (1-500 nm). Larger particles are rapidly withdrawn from the vascular compartment by the phagocytic cells of the reticuloendothelial system, limiting their ability to react with a limited number of sites on the desired target. Magnetic particles preferably have a narrow size distribution, e.g., do not have a small percentage of large particles which can occlude capillaries.

(2) Biodegradability. To be useful as a clinical diagnostic tool, magnetic particles preferably can be broken down and excreted or broken down and utilized by the body. Materials like polystyrene, while useful in the synthesis of magnetic particles for cell sorting, generally cannot be used in parenteral, clinical applications. The most common type of particle used for imaging applications are polymer coated iron oxides, with dextran or modified dextran being most often employed.

(3) Safety. The magnetic particles should be generally non-toxic. Typically, the safety factor (the dose used for imaging divided by the dose killing 50% of a group of animals) is greater than 100 and preferably greater than 1000. Toxicity may also include not only the generation of reversible or irreversible tissue damage, but also the induction of transient but annoying physiological reactions in selected subjects (such as humans) taking the preparation. These include fever, urticaria, mild pain, vomiting, and the like. To be useful as a clinical diagnostic agent, such as an MR imaging agent, the magnetic particle preferably produces no discernable physiological response, except for the desired diagnostic information, in individuals taking preparation.

(4) Stability. To be used as a parenteral agent, the particle preferably maintains its size distribution during a storage period, which, for practical commercial reasons, is typically longer than 6 months and preferably as long as two years, but may be shorter, depending upon the intended application. Instability, evident as the growth in the number of large particles in the preparation, can result in particle induced toxicity.

A wide variety of conjugating strategies have been employed to couple proteins to each other and can be adapted to couple Annexins, e.g., Annexin V and annexin V-128 to magnetic particles, as would be understood to one skilled in the art. Many of these reagents consist of an N-hydroxysuccinimide ester, which reacts with an amine, and a second moiety that reacts with a sulfhydryl group. A wide selection of bifunctional conjugating reagents, such as SPDP, SMCC, SATA and SIAt are available from Piece Chemical Company. Detailed procedures for their use are available from the Piece Chemical web site (see http://www.piercenet.com).

Administration of the annexin-coupled contrast agents is generally as described above for radiolabeled annexin.

Optical Imaging

In yet another aspect, the present disclosure provides methods for imaging pain and/or stress in a subject in vivo by administering to the subject an optical imaging composition comprising annexin coupled to an optically active molecule; illuminating the subject with a light source; and visually monitoring the presence of the optical imaging composition in the subject, thereby obtaining an image, where the image is a representation of pain and/or stress in the mammalian subject.

Optically active molecules useful in practicing the present disclosure are preferably biologically compatible, such as, but not limited to, fluorescent dyes (such as, but not limited to, fluorescein), luminescent molecules (such as, but not limited to, luminol), and bioluminescent molecules (such as, but not limited to, luciferase, luciferin, and aequorin). Many of these molecules, for instance fluorescein, can be visualized during optical evaluations such as endoscopy, bronchoscopy, peritonoscopy, direct visualization, surgical microscopy and retinoscopy.

Other examples of optically active agents that could be linked to annexin include, but are not limited to, PHOTOFRIN®, Lutrin, ANTRIN®, FOSCAN®, aminolevulinic acid, aluminum (III) phthalocyanine tetrasulfonate, Hypericin, verteporfin, and methylene blue dye.

Coupling of annexin to optically active molecules may be performed using any of the art known techniques, e.g., those described in U.S. Pat. No. 5,312,922; U.S. Pat. No. 5,928,627; U.S. Pat. No. 6,096,289; Weir, ed., Handbook of Experimental Immunology, Vol. 1, Chapter 28, pp. 28.1-28.21, Oxford, Blackwell Scientific, 1986, the entire contents of each of which are incorporated herein by reference.

Administration of the annexin-coupled optically active molecules is generally as described above for radiolabeled annexin.

Therapeutic Compositions

The present disclosure also provides therapeutic compositions for treating pain and/or stress in a subject and methods for treating pain and/or stress in a patient by administering a therapeutic composition of the disclosure.

Generally described, the therapeutic compositions comprise annexin coupled to an analgesic compound. Such compounds include those now known and those to be discovered. Exemplary analgesic compounds include, but are not limited to, non-steroidal anti-inflammatory drugs (NSAIDs), including salicylates, paracetamol (e.g., acetaminophen), and narcotics/opioids.

The compositions are generally administered in an amount effective to treat the pain and/or stress, as evidenced by the regression of symptoms and/or by taking additional images as described in the present disclosure to determine a change in the uptake of labeled annexin.

Such compositions may be administered via various routes of administration, including those described above for delivery of labeled annexin. The dosages are generally similar to or the same as the dosage amounts for the respective analgesic compound when not coupled to annexin.

Dosage Forms

The composition, shape, and type of dosage forms of the imaging and therapeutic compositions of the disclosure typically vary depending on their use. For example, a parenteral dosage form may contain smaller amounts of the active ingredient than an oral dosage form used to treat the same condition or disorder. These and other ways in which specific dosage forms encompassed by this disclosure vary from one another will be readily apparent to those skilled in the art (See, e.g., Remington's Pharmaceutical Sciences, 18th ed., Mack Publishing, Easton, Pa. (1990)).

For the imaging and/or therapeutic compositions of the present disclosure the labeled annexin (labeled with a radionuclide, contrast agent, or optical agent) or annexin coupled to an analgesic agent is typically suspended in a suitable delivery vehicle/pharmaceutically acceptable carrier, such as sterile saline. The vehicle may also contain stabilizing agents, carriers, excipients, stabilizers, emulsifiers, and the like, as is recognized in the art.

A "pharmaceutically acceptable carrier" refers to a biocompatible solution, having due regard to sterility, pH, isotonicity, stability, and the like and can include any and all solvents, diluents (including sterile saline, Sodium Chloride Injection, Ringer's Injection, Dextrose Injection, Dextrose and Sodium Chloride Injection, Lactated Ringer's Injection and other aqueous buffer solutions), dispersion media, coatings, antibacterial and antifungal agents, isotonic agents, and the like. The pharmaceutically acceptable carrier may also contain stabilizers, preservatives, antioxidants, or other additives, which are well known to one of skill in the art, or other vehicles as known in the art.

Typical compositions and dosage forms of the compositions of the disclosure can include one or more excipients. Suitable excipients are well known to those skilled in the art of pharmacy or pharmaceutics, and non-limiting examples of suitable excipients are provided herein. Whether a particular excipient is suitable for incorporation into a composition or dosage form depends on a variety of factors well known in the art including, but not limited to, the way in which the dosage form will be administered to a patient. For example, oral dosage forms, such as tablets or capsules, may contain excipients not suited for use in parenteral dosage forms. The suitability of a particular excipient may also depend on the specific active ingredients in the dosage form. For example, the decomposition of some active ingredients can be accelerated by some excipients, such as lactose, or by exposure to water. Active ingredients that include primary or secondary amines are particularly susceptible to such accelerated decomposition.

The disclosure encompasses compositions and dosage forms of the compositions of the disclosure that can include one or more compounds that reduce the rate by which an active ingredient will decompose. Such compounds, which are referred to herein as "stabilizers," include, but are not limited to, antioxidants such as ascorbic acid, pH buffers, or salt buffers. In addition, pharmaceutical compositions or dosage forms of the disclosure may contain one or more solubility modulators, such as sodium chloride, sodium sulfate, sodium or potassium phosphate, or organic acids. An exemplary solubility modulator is tartaric acid.

Like the amounts and types of excipients, the amounts and specific type of active ingredient in a dosage form may differ depending on various factors. Dosage ranges for annexin and the various imaging agents (radionuclides, contrast agents, optical imaging agents) are set forth above and/or are known to those of skill in the art. Dosage ranges for analgesic compounds will be within the ranges typically employed for such compounds, as known to one of skill in the art. It will be understood, however, that the total daily usage of the compositions of the present disclosure will be decided by the attending physician or other attending professional within the scope of sound medical judgment. The specific effective dose level for any particular host will depend upon a variety of factors, including for example, the activity of the specific composition employed; the specific composition employed; the age, body weight, general health, sex, and diet of the host; the time of administration; the route of administration; the rate of excretion of the specific compound employed; the duration of the treatment; the existence of other drugs used in combination or coincidental with the specific composition employed; and like factors well known in the medical arts. For example, it is well within the skill of the art to start doses of the composition at levels lower than those required to achieve the desired effect and to gradually increase the dosage until the desired effect is achieved.

For the methods of imaging pain and stress of the present disclosure, preferably, a detectably effective amount of the imaging composition of the present disclosure is administered to a subject. In accordance with the present disclosure, "a detectably effective amount" of the imaging composition of the present disclosure is defined as an amount sufficient to yield an acceptable image using equipment that is available for clinical use. A detectably effective amount of the imaging composition of the present disclosure may be administered in more than one dosage. The detectably effective amount of the imaging composition of the present disclosure can vary according to factors such as the degree of susceptibility of the individual, the age, sex, and weight of the individual, idiosyncratic responses of the individual, the dosimetry, and the like. Detectably effective amounts of the imaging composition of the present disclosure can also vary according to instrument and film-related factors. Optimization of such factors is well within the level of skill in the art.

Kits

The present disclosure also provides kits including a pharmaceutically acceptable carrier and an imaging composition including annexin coupled to a biocompatible radionuclide. In certain embodiments, the kit includes the reaction precursors to be used to generate the imaging composition upon combination of annexin with a radiolabeled precursor. The kits provided by the present disclosure further include indicia including at least one of: instructions for using the composition to image a subject or a region of the subject to identify the location and/or intensity of pain experienced by the subject, and instructions for using the composition to image a subject or a region of the subject to identify the location and/or intensity of stress experienced by the subject.

In certain preferred embodiments, the present disclosure provides a kit including from about 5 to 20 mCi of an imaging composition including radiolabeled annexin in combination with a pharmaceutically acceptable carrier. The imaging composition and carrier may be provided in solution or in lyophilized form. When the imaging composition and carrier of the kit are in lyophilized form, the kit may optionally contain a sterile and physiologically acceptable reconstitution medium such as water, saline, buffered saline, and the like.

EXAMPLES

Now having described the embodiments of the compositions and methods for in vivo imaging of pain and/or stress in a subject and methods and compositions for treating pain and/or stress in a subject in general, the following examples describe certain embodiments of compositions and methods for in vivo imaging of pain and/or stress in a subject and methods and compositions for treating pain and/or stress in a subject. While such embodiments are described in connection with Examples 1-7 and the corresponding text and figures, there is no intent to limit the embodiments of the present disclosure to these descriptions. On the contrary, the intent is to cover all alternatives, modifications, and equivalents included within the spirit and scope of embodiments of the present disclosure.

Example 1

Preparation of Labeled Annexin

Protein production and fluorescence labeling: Recombinant wild-type human annexin V was produced from plasmid pET12a-PAP1 in *E. coli* strain BL21(DE3) as described in Wood, et al., *Increased erythrocyte phosphatidylserine exposure in sickle cell disease: Flow-cytometric measurement and clinical associations*, Blood 88 (1996) 1873-1880 (incorporated by reference herein) and labeled with FITC as described in Tait, et al., *Phospholipid binding properties of human placental anticoagulant protein-I, a member of the lipocortin family*, J. Biol. Chem. 264 (1989) 7944-7949 (incorporated by reference herein). Recombinant annexin V-128 was produced from plasmid pJ128 in *E. coli* strain Tuner(DE3)pLacI as described in Smith, et al., *Essential role of B-helix calcium binding sites in annexin V-membrane binding*, J Biol Chem. 2004 Sep. 24; 279(39):40351-7 (incorporated by reference herein) and labeled with IAF as described in Tait, et al., *Measurement of the affinity and cooperativity of annexin V-membrane binding under conditions of low membrane occupancy*, Anal Biochem. 2004 Jun. 1; 329(1):112-9 (incorporated by reference herein). Annexin-V-128 (SEQ. ID. NO: 1) has an amino-terminal extension of Ala-Gly-Gly-Cys-Gly-His (amino acids 1 to 6 of SEQ. ID. NO: 1) added to the wild-type sequence. The expression plasmids are available from the authors. IAF-annexin V-128 was purified by anion-exchange chromatography at pH 8.0 on a MonoQ HR5/5 column as described in Smith, et al., (2004). The degree of labeling in each fraction was determined from the ratio of absorbance measurements at 494 nm and protein measurement by the BCA assay (Pierce, Rockford, Ill.).

Radiolabeling: In preparation for technetium labeling, protein (0.6 mg) was diluted with PBS pH 7.4 to a final volume of 0.2 ml and reduced with 1 mM dithiothreitol at 37° C. for 15 min under anaerobic conditions. The protein was then applied to a Sephadex G-25 column (NAP-5; Pharmacia, Piscataway, N.J.), which had been pre-equilibrated with deoxygenated buffer (20 mM trisodium citrate, pH 5.4, 100 mM NaCl), and the breakthrough (0.2 ml) was discarded. Elution was performed with the same buffer; the first 0.5 ml of eluate was discarded, and the subsequent 0.5 ml, containing the protein, was collected in argon-flushed glass vials. Aliquots of 0.1 ml (containing 0.1 mg protein, 0.59 mg trisodium citrate, and 0.58 mg NaCl) were stored frozen at −20° C. in glass vials with teflon-sealed screw caps. Just prior to use for labeling, a vial was thawed and mixed. Tin reagent was prepared as described in Larsen, et al., *Technetium complex of tricine: useful precursor for the 99mTc labeling of hydrazino nicotinamide modified proteins*, J. Labelled Compds. Radiopharm. 35, 1-2 (1994) (incorporated by reference herein). Each vial of lyophilized reagent contained 5 mg of sodium glucoheptonate, 0.128 mg $SnCl_2 2H_2O$, and 0.128 mg of sodium gentisate. Just prior to use, the vial was reconstituted with 0.2 ml of deoxygenated water.

For in vivo studies, 99 mTc-annexin V-128 was prepared as described in Tait, et al., *Structural requirements for in vivo detection of cell death with 99mTc-Annexin V*, J. Nucl. Med. 46, 807-815 (2005) (incorporated by reference herein). $99mT_cO_4$ 5-10 mCi in ~0.1 ml of 0.9% NaCl was diluted with 0.6 ml deoxygenated PBS pH 7.4. To this, 0.005 ml of tin reagent and 0.05 ml (0.05 mg) of reduced protein was added. After a 60-min anaerobic incubation at 37° C., the reaction mixture was applied to a Sephadex G-25 column (Pharmacia PD-10) and eluted in 1-ml fractions with 10 ml PBS pH 7.4; fractions 3 and 4 contained the labeled protein and were pooled for in vivo use. Percent incorporation of technetium was routinely 90%, corresponding to a specific activity of about 100 µCi/µg.

Example 2

In Vivo Pain Studies

Wistar or Swiss-Webster mice used in the experiment were either young, 8-10 weeks in age, or old, 4-6 months in age. Pain was induced by intrapaw injection of a constant noxious stimulus induced by subcutaneous injection of CFA (bovine collagen dissolved in Freund's Adjuvant), in either the forepaw or hindpaw. Approximately 24 hours after intrapaw injection, imaging was performed. Pain and control mice were injected, via tail vein, with of 10 to 200 µg/kg of radiolabeled annexin V-128, and after approximately one hour, imaging was performed by microSPECT and autoradiography.

Imaging showed that uptake of radiolabeled annexin V in the spine was 3 to 4 times the uptake seen in non-pain control mice, and uptake was 5 to 7 times greater in the brain. FIG. 1 illustrates uptake of radiolabeled annexin V 128 in pain versus control mice. FIG. 1A illustrates the spinal cord 10 and the nerve to the left hindpaw 12 in a normal mouse, while FIG. 1B illustrates the spinal cord 10 and nerve 12 to the inflamed left hindpaw in a pain-induced mouse. FIG. 5 shows microSPECT coronal images illustrating uptake of radiolabeled annexin V-128 in intact spinal cords of control mice (FIG. 5A) and mice with pain induced in the left forepaw (FIG. 5B) or left hindpaw (FIG. 5C).

Figure 2:
FIG. 2 illustrates the uptake of fluorescently-labeled annexin V in rat spinal cords and brains for control rats (A) and rats with pain induced in either the left front (B) or left hind (C) paw.

The above results were confirmed by fluorescence imaging with IAF-labeled annexin V 128 in Sprague Dalwey rats 8 to 12 weeks in age. Pain was induced as described above for mice. For fluorescent imaging, the pain and control rats were injected with 100-200 ug/kg of IAF-annexin V-128. A dose of 2 to 10 mCi of tracer (500 to 700 µl volume) was injected via tail vein one hour before sacrifice. Results are shown in FIG. 2, which illustrates the uptake of fluorescently-labeled Annexin V 128 in the spinal cords and brains of control rats (FIG. 2A) and those with pain induced in the forepaw (FIG. 2B) or in the hindpaw (FIG. 2C). In the figures, green is background and red indicates a positive signal. FIG. 6 shows SPECT/CT images of rat spines illustrating uptake of labeled annexin 24 hours after paw injection to induce pain. FIG. 6A shows a microCT image, FIG. 6B shows a microSPECT image, and FIG. 6B shows a SPECT/CT fusion image.

Example 3

In Vivo Stress Studies

Stress can be induced in animals by performing tail vein injections while the animals are awake. In contrast, control animals are anesthetized using 2-3% isoflurane gas anesthesia (administered via inhalation) immediately prior to tail vein injections.

In the present Example, 8-10 week-old and 4-6 month-old male Swiss Webster mice were studied. Stress was induced in animals by placing awake animals in a commercially-available mouse restrainer that is used specifically for holding mice for tail vain injections. After positioning the mice within the confined space of the restrainer, mice were immediately injected via tail vein with 10 to 200 µg/kg of radiolabeled annexinV-128. Stressed mice experienced a 1 minute time period within the restrainer. Control animals were anesthetized in a gas chamber prior to injection and were continuously anesthetized during the tail vein injection.

Figure 3:
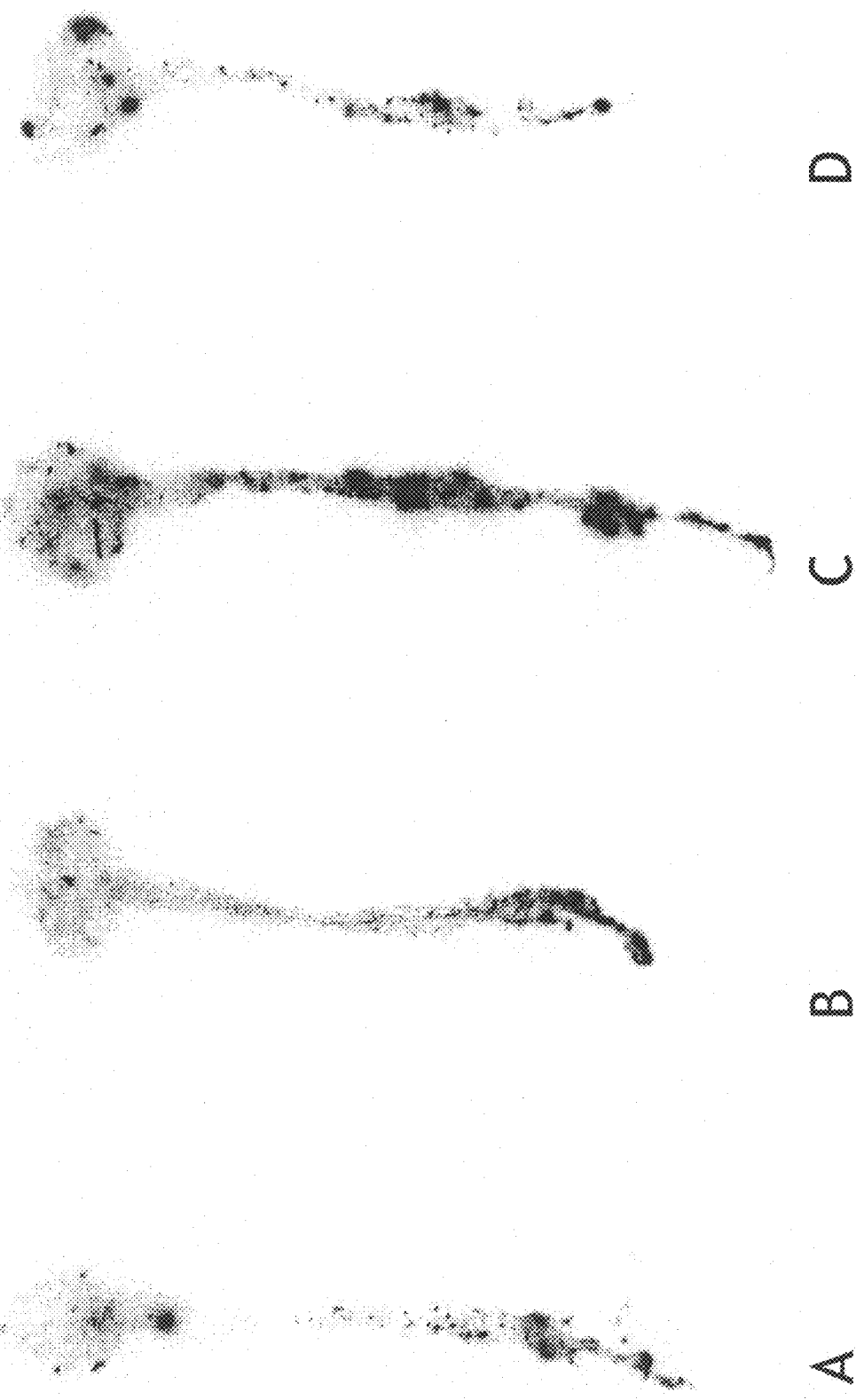
FIG. 3 shows the uptake of radiolabeled annexin V 128 in mouse spinal cords for old (D) and young (A and B) control mice and an old stress induced mouse (C).

In both the experimental and control groups, animals were euthanized after one hour and central nervous system tissues was harvested for autoradiography. Spinal cord and brain uptake of radiolabeled Annexin V 128 in stress versus control mice are demonstrated in FIGS. 3 and 4, respectively. Dramatically increased uptake can be seen in the spinal cord (4-5 fold increase) and brain (2 to 3-fold increase) of a stressed older mouse (FIGS. 3C and 4C) when compared to younger controls (FIGS. 3A, 3B, 4A and 4B) and old (FIGS. 3D and 4D) controls.

Example 4

Attachment of Annexin V to Dextran Coated Magnetic Iron Oxides Through the Use of Periodate Periodate treatment of the dextran coated magnetic particle produces an aldehyde, which forms a Schiff base with the amines of the Annexin V. The complex is stabilized by treatment with sodium borohydride.

A dextran coated superparamagnetic iron oxide nanoparticle was synthesized according to the methods of Molday (1982) *J. Immunol. Methods* 52, 353, which is incorporated herein by reference. Iron oxide (10 mg Fe in about 1 mL of water) and purified Annexin V were dialyzed against sodium acetate (0.01 M, pH 6). Annexin V was purified by the method of Wood (1996) *Blood* 88, 1873, which is incorporated herein by reference. The amount of Annexin V can be varied from 1 to about 50 mg, preferably 5-10 mg of protein. At lower amounts the ratio of protein to iron on the resulting magnetic nanoparticle will be lower, but the offered protein will couple more efficiently. At higher amounts of protein, the ratio of protein to iron on the resulting nanoparticle will be higher, but the percent of protein coupled will be lower.

Freshly made sodium periodate (50 mg/mL, 0.2 mL) was added to the iron oxide. The mixture was then incubated for 30 minutes at room temperature in the dark, and dialyzed against 0.15 M NaGI. The oxidized magnetic iron oxide was then mixed with the Annexin V and the pH adjusted by the addition of 100 µl of 0.2 M sodium bicarbonate, pH 9.5. The mixture was incubated for 3 hours with stirring. Freshly made sodium cyanoborohydride was then added (25 mg/mL, 0.2 mL) and the mixture was incubated for 6 hours at room temperature. The annexin V-magnetic nanoparticle can be separated from the unreacted annexin by a variety of sized based separation methods. These include gel filtration, ultrafiltration or magnetic separation.

Example 5

Attachment of Annexin V with a Sulfhydryl Group to Amino CLIO

The amino-CLIO nanoparticle was made as described in Josephson (1999) *Bioconjug. Chem.* 10, 186. Annexin V with a sulfhydryl group added through mutagenesis (Tait (2000) *Bioconjug Chem* 11, 918) was employed. To 1.2 mL of amino-CLIO in (30 mg Fe) was added 1.2 mL of 0.1 M phosphate buffer, pH 7.4, and 2 mL of N-succinimidyl 3-(2-pyridyldithio)propionate (SPDP, 25 mM) (Molecular Biosciences, Boulder, Colo.) in DMSO. The mixture was allowed to stand for 60 minutes at room temperature. Low molecular impurities were removed by PD-10 columns (Sigma Chemical, St-Louis, Mo.) equilibrated with 0.01 M Tris and 0.02 M citrate, pH 7.4 buffer.

Between 2 and 50 mg of Annexin V was subsequently added to 10 mg Fe of the SPDP activated nanoparticle at room temperature, and the mixture was allowed to stand overnight. The Annexin V-magnetic nanoparticle can be separated from the unreacted annexin by a variety of sized based separation methods.

Example 6

Reaction of Annexin V to Add a Sulfhydryl Group, Followed by Reaction with Amino CLIO A sulfhydryl group was added to the annexin (obtained as in Example 4) by use of the reagent SATA following the manufacturer's instructions, Pierce Chemical Company. Amino-CLIO was reacted with SPDP as in Example 2 and then reacted with the SAT A reacted annexin.

Example 7

Attachment of Annexin V to a BSA Coated Magnetic Particle

BSA coated magnetic particles were made as described in U.S. Pat. No. 4,795,698 (which is incorporated by reference herein). Some of the amine groups of the BSA coating of the magnetic particle are converted to sulfydryl groups by use of the reagent SPDP (see Example 5). SPDP or SATA can then be used to add one or more sulfydryl groups on Annexin V. After treatment of the Annexin V with DTT, to expose a sulfhydryl group, the protein is reacted with the magnetic particle.

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure and the following claims.

We claim:

1. A method of imaging pain in a subject in vivo comprising:
   administering to the subject an imaging composition comprising a labeled annexin including annexin coupled to a biocompatible radionuclide; and
   measuring radiation emission from the radionuclide in the subject to construct an image of radiation emission, wherein the image is a representation of pain in the subject.

2. The method of claim 1, wherein the radionuclide is selected from the group consisting of Iodine 123, Iodine 131, Gallium 67, Indium 111, Fluorine 18, and Technetium 99 m (Tc99m).

3. The method of claim 2, wherein the radionuclide is Tc99m to form Tc99m-labeled annexin.

4. The method of claim 3, wherein the Tc99m is linked to the annexin via hydrazino nicotinamide (HYNIC) or via the internal radionuclide chelating site of annexin V-128.

5. The method of claim 3, wherein the amount of Tc99m-labeled annexin administered results in a dose of about 5 to 20 mCi.

6. The method of claim 1, wherein the radiation is measured with a radiation detector device and wherein the radiation detection device is a gamma ray detector device and the radiation emission is gamma ray emission.

7. The method of claim 6, where the gamma ray detector device is a gamma scintillation camera.

8. The method of claim 6, wherein the measuring of gamma ray emission to construct the image is done about 5 minutes to 2 hours after administration of the labeled annexin.

9. The method of claim 8, wherein the measuring of gamma ray emission to construct the image is done about 1 hour after administration of the labeled annexin.

10. The method of claim 1, further comprising repeating the step of measuring radiation emission at selected intervals, wherein said repeating is effective to track changes in the intensity of radiation emission from the subject over time, reflecting changes in the intensity of the pain.

11. The method of claim 1, further comprising repeating the step of measuring radiation emission at selected intervals, wherein said repeating is effective to track changes in the localization of radiation emission in the subject over time, reflecting changes in the location of cells reacting to pain stimulus.

12. The method of claim 1, wherein the annexin is annexin V.

13. The method of claim 1, wherein the annexin is annexin V-128.

14. The method of claim 1, wherein the amount of labeled annexin administered is less than about 300 μg protein/kg.

15. The method of claim 14, wherein the amount of labeled annexin administered is about 1 to 10 μg protein/kg.

16. The method of claim 1, wherein the labeled annexin is administered via a route of administration selected from at least one of the following: intravenously, intraperitoneally, intrathecally, intrapleurally, intralymphatically, and intramuscularly.

17. The method of claim 1, wherein the radiation emission is measured from a region of the subject, wherein the region is in an organ of the subject or a portion thereof.

18. The method of claim 17, wherein the region is selected from at least one of the following: the head of the subject or a portion thereof and the spine of the subject or a portion thereof.

19. The method of claim 1, wherein the radiation is measured with a radiation detector device and wherein the radiation detection device is a positron emission detector device.

20. A method of imaging pain in a subject in vivo comprising:
    administering to the subject an imaging composition comprising a labeled annexin including annexin coupled to a contrast agent; and
    obtaining a magnetic resonance image, wherein said image is a representation of pain in said subject.

21. The method of claim 20, wherein the contrast agent is selected from at least one of the following: a paramagnetic agent, a gadolinium-chelating group complex, a gadolinium-diethylenetriamine penta-acetic acid, a superparamagnetic agent, a metal oxide, an iron oxide, a polymer coated metal oxide, and a dextran coated iron oxide.

22. The method of claim 20, wherein the annexin is annexin V.

23. The method of claim 20, wherein the annexin is annexin V-128.

24. The method of claim 20, wherein the magnetic resonance image is obtained about 5 minutes to 2 hours after the administration of the magnetic resonance imaging composition.

25. The method of claim 20, wherein the magnetic resonance image is obtained about 12 to 30 hours after the administration of the magnetic resonance imaging composition.

26. The method of claim 20, further comprising obtaining a magnetic resonance image at a plurality of time points, thereby monitoring changes in the number of cells responding to pain.

27. The method of claim 20, further comprising obtaining a magnetic resonance image at a plurality of time points, thereby monitoring changes in the location of cells responding to pain.

28. The method of claim 20, wherein the magnetic resonance imaging composition is administered at a concentration of about 1 to 500 μg protein/kg.

29. The method of claim 20, wherein the magnetic resonance imaging composition is administered at a concentration of less than about 300 μg protein/kg.

30. The method of claim 20, wherein the magnetic resonance imaging composition is administered via a route of administration selected from one of the following: intravenously, intraperitoneally, intrathecally, intrapleurally, intralymphatically, and intramuscularly.

31. The method of claim 20, wherein the magnetic resonance is imaged from a region of the subject, wherein the region is in an organ of the subject or a portion thereof.

32. The method of claim 31, where said region is selected from at least one of the following: the head of the subject or a portion thereof and the spine of the subject or a portion thereof.

33. The method of claim 3, wherein the Tc99m is linked to the annexin via the internal radionuclide chelating site of annexin V-128.

34. The method of claim 3, wherein the amount of Tc99m-labeled annexin administered results in a dose of up to about 20 mCi.

* * * * *

SEQUENCE LISTING

<160> NUMBER OF SEQ ID NOS: 1

<210> SEQ ID NO 1
<211> LENGTH: 325
<212> TYPE: PRT
<213> ORGANISM: Homo sapiens

<400> SEQUENCE: 1

```
Ala Gly Gly Cys Gly His Ala Gln Val Leu Arg Gly Thr Val Thr Asp
1               5                   10                  15

Phe Pro Gly Phe Glu Asp Arg Ala Asp Ala Glu Thr Leu Arg Lys Ala
            20                  25                  30

Met Lys Gly Leu Gly Thr Asp Glu Glu Ser Ile Leu Thr Leu Leu Thr
        35                  40                  45

Ser Arg Ser Asn Ala Gln Arg Gln Glu Ile Ser Ala Ala Phe Lys Thr
    50                  55                  60

Leu Phe Gly Arg Asp Leu Leu Asp Asp Leu Lys Ser Glu Leu Thr Gly
65                  70                  75                  80

Lys Phe Glu Lys Leu Ile Val Ala Leu Met Lys Pro Ser Arg Leu Tyr
                85                  90                  95

Asp Ala Tyr Glu Leu Lys His Ala Leu Lys Gly Ala Gly Thr Asn Glu
            100                 105                 110

Lys Val Leu Thr Glu Ile Ile Ala Ser Arg Thr Pro Glu Glu Leu Arg
        115                 120                 125

Ala Ile Lys Gln Val Tyr Glu Glu Tyr Gly Ser Ser Leu Glu Asp
    130                 135                 140

Asp Val Val Gly Asp Thr Ser Gly Tyr Tyr Gln Arg Met Leu Val Val
145                 150                 155                 160

Leu Leu Gln Ala Asn Arg Asp Pro Asp Ala Gly Ile Asp Glu Ala Gln
                165                 170                 175

Val Glu Gln Asp Ala Gln Ala Leu Phe Gln Ala Gly Glu Leu Lys Trp
            180                 185                 190

Gly Thr Asp Glu Glu Lys Phe Ile Thr Ile Phe Gly Thr Arg Ser Val
        195                 200                 205

Ser His Leu Arg Lys Val Phe Asp Lys Tyr Met Thr Ile Ser Gly Phe
    210                 215                 220

Gln Ile Glu Glu Thr Ile Asp Arg Glu Thr Ser Gly Asn Leu Glu Gln
225                 230                 235                 240

Leu Leu Leu Ala Val Val Lys Ser Ile Arg Ser Ile Pro Ala Tyr Leu
                245                 250                 255

Ala Glu Thr Leu Tyr Tyr Ala Met Lys Gly Ala Gly Thr Asp Asp His
            260                 265                 270

Thr Leu Ile Arg Val Met Val Ser Arg Ser Glu Ile Asp Leu Phe Asn
        275                 280                 285

Ile Arg Lys Glu Phe Arg Lys Asn Phe Ala Thr Ser Leu Tyr Ser Met
    290                 295                 300
```

```
Ile Lys Gly Asp Thr Ser Gly Asp Tyr Lys Lys Ala Leu Leu Leu Leu
305                 310                 315                 320

Ser Gly Glu Asp Asp
                325
```